(12) United States Patent
Angelides

(10) Patent No.: US 11,315,686 B2
(45) Date of Patent: Apr. 26, 2022

(54) INDIVIDUALIZED CARE MANAGEMENT SYSTEM BASED ON DIGESTIVE ACTIVITY

(71) Applicant: Vivante Health, Inc., Houston, TX (US)

(72) Inventor: Kimon Angelides, Houston, TX (US)

(73) Assignee: Vivante Health, Inc., Houston, TX (US)

( * ) Notice: Subject to any disclaimer, the term of this patent is extended or adjusted under 35 U.S.C. 154(b) by 112 days.

(21) Appl. No.: 16/145,593

(22) Filed: Sep. 28, 2018

(65) Prior Publication Data

US 2020/0051693 A1 Feb. 13, 2020

Related U.S. Application Data

(60) Provisional application No. 62/715,460, filed on Aug. 7, 2018.

(51) Int. Cl.
*G16H 50/00* (2018.01)
*G16H 50/20* (2018.01)
(Continued)

(52) U.S. Cl.
CPC ............... *G16H 50/20* (2018.01); *C12Q 1/04* (2013.01); *G01N 33/4833* (2013.01);
(Continued)

(58) Field of Classification Search
None
See application file for complete search history.

(56) References Cited

U.S. PATENT DOCUMENTS 4,542,640 A * 9/1985 Clifford ............. G01N 33/0031
422/98
4,744,953 A 5/1988 Wolf et al.
(Continued)

FOREIGN PATENT DOCUMENTS

CN 201580032981 2/2017
EP 0647427 4/1995
(Continued)

OTHER PUBLICATIONS

Ou, J. Z. et al; "Human intestinal gas measurement systems: in vitro fermentation and gas capsules"; Trends in Biotechnology, Apr. 2015, vol. 33, No. 4; p. 208-213 (Year: 2015).*
(Continued)

*Primary Examiner* — Lori A. Clow
*Assistant Examiner* — Marie Archer
(74) *Attorney, Agent, or Firm* — Eric P. Mirabel, JD, LLM

(57) ABSTRACT

Embodiments of this invention include systems and methods for developing individualized dietary and health improvement plans based on an individual's intestinal microbiome and digestive activity. More particularly, the invention is related to a system providing a hydrogen and/or methane sensor device and a wireless platform in communication with the sensor device to periodically analyze the individual's metabolic activity in correlation with their gut microbiome and a personal database to provide personalized feedback to the individual of treatment plans and general techniques that can be used to improve the individual's general health and well being. The systems and methods further include a system for analyzing the hydrogen and/or methane levels in the individual's exhalations or flatulence in light of the individual's intestinal microbiome. This analysis uses bioinformatics to relate alterations in hydrogen (Continued)

and/or methane levels to the individual's intestinal microbiome and personal diet and tolerances/intolerances to identify and communicate real time dietary suggestions and general dietary and health treatment plans. The relationship of the bioinformatics and alterations in hydrogen and/or methane levels is also used to infer drug effectiveness. Such general dietary guidance, health treatment plans, and drug effectiveness contribute to an overall improvement in a person's general health and well being.

14 Claims, 8 Drawing Sheets

(51) Int. Cl.
G16H 40/63 (2018.01)
G16H 10/40 (2018.01)
G01N 33/483 (2006.01)
G01N 33/497 (2006.01)
C12Q 1/04 (2006.01)

(52) U.S. Cl.
CPC .......... *G01N 33/497* (2013.01); *G16H 10/40* (2018.01); *G16H 40/63* (2018.01); *G01N 2033/4975* (2013.01)

(56) References Cited

U.S. PATENT DOCUMENTS

| | | | |
|---|---|---|---|
| 6,171,237 B1 | 1/2001 | Avitall et al. | |
| 7,914,460 B2 | 3/2011 | Melker et al. | |
| 7,935,307 B2 | 5/2011 | Angelides | |
| 7,999,232 B2* | 8/2011 | Wilson | G01N 21/39 250/339.13 |
| 8,066,640 B2 | 11/2011 | Angelides | |
| 8,211,035 B2* | 7/2012 | Melker | G01N 33/497 600/532 |
| 8,381,573 B2 | 2/2013 | Keays | |
| 8,568,309 B2 | 10/2013 | Angelides | |
| 8,812,244 B2 | 8/2014 | Angelides | |
| 2007/0073113 A1* | 3/2007 | Squilla | A61B 5/00 600/300 |
| 2008/0299009 A1 | 12/2008 | Angelides | |
| 2009/0137047 A1* | 5/2009 | Regan | G01N 35/04 436/48 |
| 2009/0264337 A1 | 10/2009 | Angelides | |
| 2010/0063408 A1 | 3/2010 | Nothacker et al. | |
| 2010/0063837 A1* | 3/2010 | Bellante | G16H 40/67 705/2 |
| 2010/0101317 A1* | 4/2010 | Ashrafzadeh | G01F 23/0061 73/149 |
| 2010/0191075 A1 | 7/2010 | Angelides | |
| 2010/0331641 A1* | 12/2010 | Bangera | G16B 5/00 600/345 |
| 2012/0029327 A1 | 2/2012 | Angelides | |
| 2012/0231431 A1 | 9/2012 | Angelides | |
| 2013/0035563 A1 | 2/2013 | Angelides | |
| 2013/0078601 A1 | 3/2013 | Angelides | |
| 2013/0187780 A1 | 7/2013 | Angelides | |
| 2014/0154653 A1 | 6/2014 | Angelides | |
| 2014/0165698 A1 | 6/2014 | Mochizuki | |
| 2014/0363794 A1 | 12/2014 | Angelides | |
| 2015/0100352 A1 | 4/2015 | Amies et al. | |
| 2015/0213193 A1* | 7/2015 | Apte | C12Q 1/6888 435/6.12 |
| 2015/0294073 A1 | 10/2015 | Angelides | |
| 2015/0313534 A1 | 11/2015 | Angelides | |
| 2015/0317913 A1 | 11/2015 | Angelides | |
| 2016/0038562 A1* | 2/2016 | Pimentel | A61P 1/04 514/5.9 |
| 2016/0283563 A1 | 9/2016 | Hodjat et al. | |
| 2017/0076630 A1 | 3/2017 | Angelides et al. | |
| 2017/0140103 A1 | 5/2017 | Angelides | |
| 2018/0271404 A1* | 9/2018 | Gupta | G01N 5/02 |
| 2018/0316781 A1* | 11/2018 | Salem | H04L 67/306 |
| 2019/0178868 A1* | 6/2019 | Shortt | G01N 33/497 |

FOREIGN PATENT DOCUMENTS

| | | |
|---|---|---|
| EP | 2891883 | 7/2015 |
| EP | 3330708 | 6/2018 |
| JP | 2013192860 | 9/2013 |
| JP | 6315316 | 4/2018 |
| KR | 20180043832 | 4/2018 |

OTHER PUBLICATIONS

Belson, A., Shetty, A.K., Yorgin, P.D. et al. Colonic Hydrogen Elimination and Methane Production in Infants with and Without Infantile Colic Syndrome. Dig Dis Sci 48, 1762-1766 (2003). (Year: 2003).*
Pimentel, M., Mathur, R. & Chang, C. Gas and the Microbiome. Curr Gastroenterol Rep 15, 356 (2013). (Year: 2013).*
Shin, W.; "Medical applications of breath hydrogen measurements"; Anal Bioanal Chem (2014) 406:3931-3939. (Year: 2014).*
Di Stefano, M. et al; "Role of hydrogen and methane breath testing in gastrointestinal disease"; Digestive and Liver Disease Supplements 3 (2009) 40-43. (Year: 2009).*
Sloan, T.J. et al; (2018) "A low FODMAP diet is associated with changes in the microbiota and reduction in breath hydrogen but not colonic volume in healthy subjects". PLOS ONE 13(7): e0201410 ; p. 1-18 (Year: 2018).*
Ursell, L.K., et al.; "Defining the human microbiome". Nutr Rev. 2012;70 Suppl 1(Suppl 1):S38-S44 (Year: 2012).*
Jose, P. A. and Raj, D. "Gut microbiota in hypertension." Current opinion in nephrology and hypertension vol. 24,5 (2015): 403-9. (Year: 2015).*
Li, J., Zhao, F., Wang, Y. et al. Gut microbiota dysbiosis contributes to the development of hypertension. Microbiome 5, 14 (2017). (Year: 2017).*
Amann, A. et al; "The human volatilome: volatile organic compounds (VOCs) in exhaled breath, skin emanations, urine, feces and saliva"; J. Breath Res. 8 (2014) 034001; p. 1-17 (Year: 2014).*
Probert, C. S. J. et al; "Fecal volatile organic compounds: a novel, cheaper method of diagnosing inflammatory bowel disease?"; (2014) Expert Review of Clinical Immunology, 10:9, 1129-1131 (Year: 2014).*
Jahng, J., et al. "The effects of methane and hydrogen gases produced by enteric bacteria on ileal motility and colonic transit time." Neurogastroenterology & Motility 24.2 (2012): 185-e92 (Year: 2012).*
Levitt, Michael D., and Franz J. Ingelfinger. "Hydrogen and methane production in man." Annals of the New York Academy of Sciences 150.1 (1968): 75-81. (Year: 1968).*
TS King, et al; "Abnormal colonic fermentation in irritable bowel syndrome", The Lancet, vol. 352, Issue 9135, 1998, pp. 1187-1189. (Year: 1998).*
Roccarina, Davide, et al. "The role of methane in intestinal diseases." Official journal of the American College of Gastroenterologyl ACG 105.6 (2010): 1250-1256. (Year: 2010).*
Alcohol Breath Analyser. Nov. 4, 2018; 35 pages.
Diyatel AT570o Dgital Breath Analyzer Alcohol Tester with Replace Mouthpiece AT570 Orange Breathalyzer. 2014. p. 1-4.

* cited by examiner

INDIVIDUALIZED CARE MANAGEMENT SYSTEM BASED ON DIGESTIVE ACTIVITY

BACKGROUND OF THE INVENTION

Field of the Invention

This invention is related to systems and methods for developing individualized dietary and/or health improvement plans based on an individual's intestinal microbiome and digestive activity. More particularly, the invention is related to a system providing a hydrogen and/or methane sensor device and a wireless platform in communication with the sensor device to periodically analyze the individual's digestive and metabolic activity and advise the individual of treatment plans and general techniques that can be used to improve their eating behavior and general health and well being.

Description of the Related Art

Every hour of every day, people face a continuous series of choices. What to eat, what not to eat. As much as 74% of the American population experiences various digestive problems and/or conditions. Making wise dietary choices can be confusing, particularly if certain foods, stress, and/or exercise exacerbate the problem. For individuals with chronic digestive complications or discomfort making everyday food choices, can be extremely difficult.

Finding appropriate treatment plans for individuals facing chronic digestive complications requires a multifaceted and multidisciplinary approach. Living with the symptoms of chronic digestive complications or disease is confusing, unpredictable, and often embarrassing. Chronic digestive diseases (such as celiac disease, Crohns disease, irritable bowel syndrome, or ulcerative colitis) affect at least 70 million people. Medical regimens to address these diseases and assist in relieving symptoms are complicated and involve complicated medication regimens that are difficult and expensive to manage. Furthermore, up to 37% of patients with chronic digestive disease are admitted into an emergency room every year and 70% of such patients need some type of surgical intervention.

Thus, there is a need for individualized processes that will decrease the symptomology of patients with chronic digestive disease, reduce medical costs, enhance patient empowerment and productivity.

SUMMARY OF THE INVENTION

This invention is related to systems and methods for developing individualized dietary and health improvement plans based on an individual's intestinal microbiome and digestive activity. More particularly, the invention is related to a system providing a hydrogen and/or methane sensor device and a wireless platform in communication with the sensor device to periodically analyze the individual's own metabolic activity and the metabolic activity of the individual's microbiome in correlation with their gut microbiome and a personal database to provide personalized feedback to the individual of dietary choices and general techniques that can be used to improve the individual's dietary behavior to increase their general health and well being.

One embodiment of the invention is a care management system for a person having a chronic digestive discomfort comprising: a) a sensor device for measuring a digestive activity of the person; b) a processing unit having a data repository and a knowledge module, wherein the knowledge module is in communication with the data repository and has a set of computer program instructions for extracting, analyzing, and correlating information relevant to the digestive disease of the person; and c) a platform in communication with the sensor device, the processing unit, wherein the platform is configured to communicate with the person through an interactive portal Another embodiment of the invention is a digestive improvement kit comprising: a) an intestinal microbiome analysis based on a fecal sample of a person; b) a processing unit having a data repository and a knowledge module, wherein the knowledge module is in communication with the data repository and has a set of computer program instructions for extracting, analyzing, and correlating information relevant to the digestive disease of the person; c) a hydrogen or methane sensor device for measuring a hydrogen level in an exhalation of the person and/or a methane level of gasses emitted from the fecal sample wherein the sensor device is configured to communicate with the processing unit; and d) a platform in communication with the sensor device, the processing unit, wherein the platform is configured to communicate with the person through an interactive portal.

Yet another embodiment of the invention is a method for developing personalized dietary guidance for digestive discomfort consisting of: a) obtaining of a fecal sample from an individual; b) analyzing the fecal sample to determine an intestinal microbiome analysis of the individual; c) obtaining a base exhaled hydrogen level or methane level of the individual when the fecal sample was collected; d) collecting a personalized information database including a set of personal diet preferences and food tolerances of the individual; e) entering the intestinal microbiome analysis, the base hydrogen or methane level, and the personalized information database into a processing unit; f) collecting measurements of exhaled hydrogen levels of the individual at selected intervals; g) recording a dietary consumption profile and a digestive discomfort of the individual at the selected intervals; h) correlating changes in the exhaled hydrogen levels of the individual to the dietary consumption profile and digestive discomfort of the individual; and i) communicating personalized dietary recommendations to the individual to reduce the exhaled hydrogen level of the individual.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures and systems for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

It is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in any appropriately detailed structure.

This invention is related to systems and methods for developing individualized health improvement plans based on an individual's intestinal microbiome and digestive activity. More particularly, the invention is related to a system providing a hydrogen and/or methane sensor device and a wireless platform in communication with the sensor device to periodically analyze the individual's metabolic activity and advise the individual of eating and treatment plans and general techniques that can be used to improve their general health, digestion, and well being.

Figure 1:
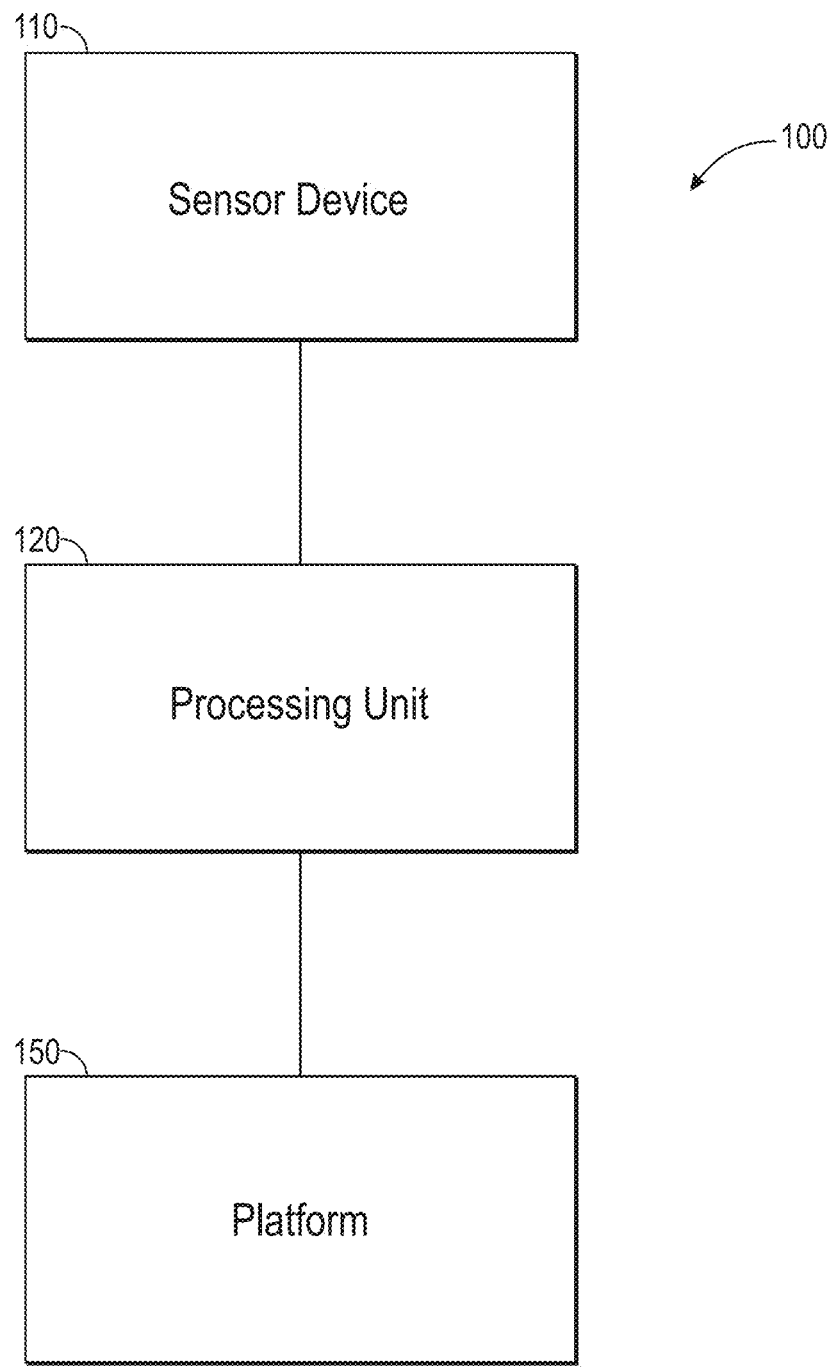
FIG. 1 is a schematic illustration of a system for providing a personalized care management system for an individual with digestive discomfort or symptoms.
Figure 2:
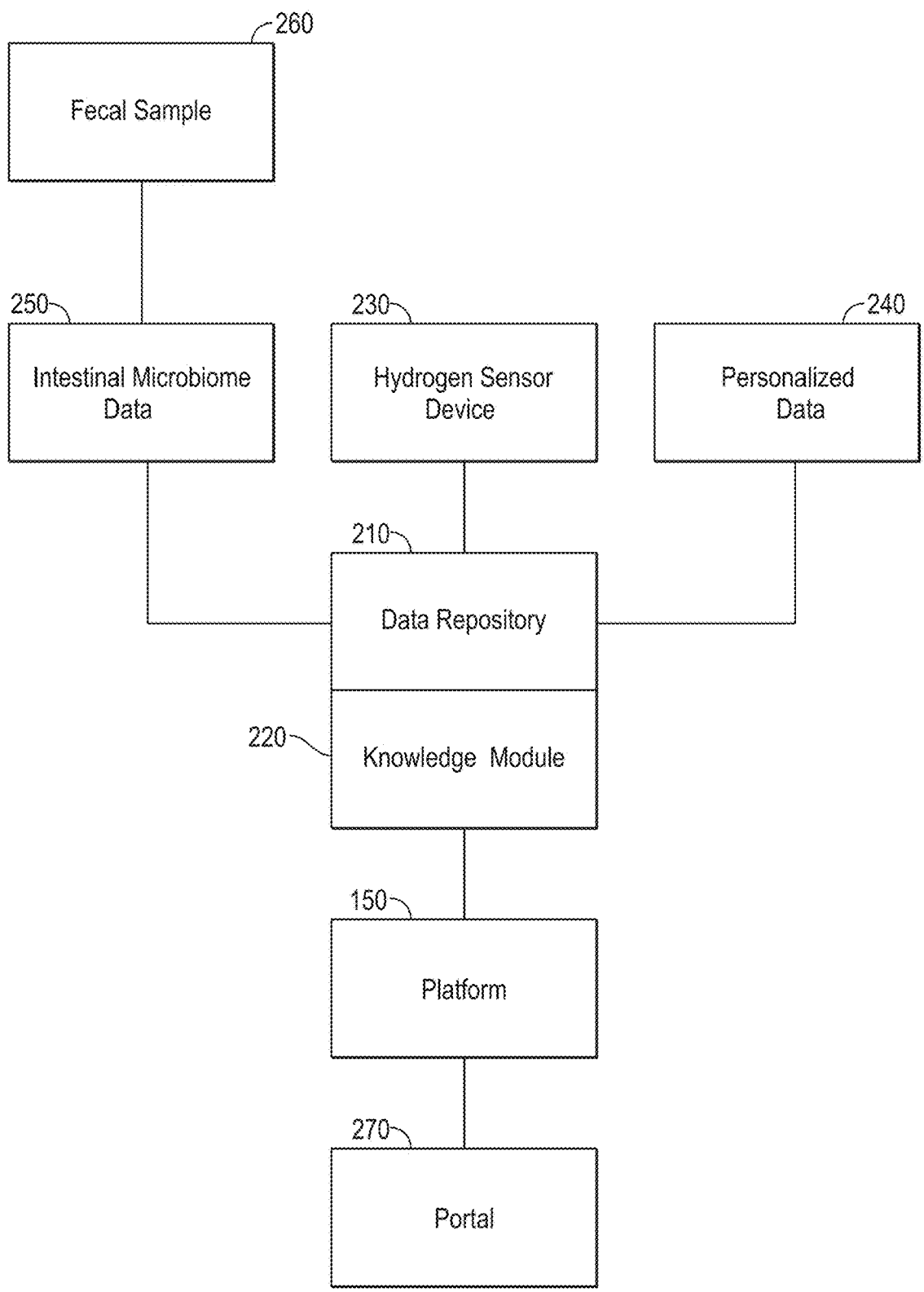
FIG. 2 is an illustration of one embodiment of a care management system.

Referring now to the drawings, and initially to FIG. 1, it is pointed out that like reference characters designate like or similar parts throughout the drawings. The Figures, or drawings, are not intended to be to scale. For example, purely for the sake of greater clarity in the drawings, component size and spacing are not dimensioned as they actually exist in the assembled embodiment.

Embodiments of the invention relate to personalized dietary and care management systems for persons having digestive complications comprising: a) a sensor device 110 for measuring a digestive activity of the person; b) a processing unit 120, wherein the processing unit comprises computer program instructions for extracting, analyzing, and correlating information relevant to the digestive complications of the person; and c) a wireless platform 150 in communication with the sensor device and the processing unit, wherein the platform is configured to periodically advise the person of needed actions as well as to provide reminders, advice and coaching.

Certain embodiments are partially implemented using a wireless biometric device that has its data automatically uploaded. This real-time data is important in order to provide immediate feedback. For example, before a meal, a person can check his gut digestive activity with a sensor device. The current digestive activity is measured through the wireless device and processed through a processing unit to extract, analyze, and correlate personalized and general information relevant to the digestive health and/or complications of the person. The processed data is then communicated to the device user as instant alerts and feedback on what foods are compatible at that instant with their digestive activity and/or what food intake is appropriate or adjustments might be necessary in order to avoid any digestive discomfort. Thus, a person can measure their real time hydrogen/methane exhalation levels and immediately and make adjustments to the amount and types of foods they should intake, similar to how a diabetic measures their blood glucose level and relates it to the desired food and/or insulin intake. In addition, the real time measure of hydrogen/methane exhalation levels, when related to a profile of a normal gut flora can be an indicator for the effectiveness of certain drugs.

Other embodiments of the invention include methods for developing personalized dietary and health advice for individuals, including those with chronic digestive discomfort or disease. Such methods include developing personalized dietary advice consisting of: a) collecting an individual's fecal sample 260 and analyzing it to determine data about the individual's intestinal microbiome, then entering such data on an intestinal microbiome 250 of an individual into a data repository 210 of the processing unit 120; b) using a hydrogen sensor device 230 to measure exhaled hydrogen levels of the individual; entering exhaled hydrogen levels into the data repository; c) entering a standardized exhaled hydrogen level of the individual into the processing unit after consumption of a standardized dose of a specific carbohydrate by the individual; d) collecting and entering personalized data 240 into the processing unit; e) collecting a set of exhaled hydrogen levels of the individual; f) correlating changes in the exhaled hydrogen levels to the intestinal microbiome and standardized measurements; g) relating the correlated changes to the personalized data; h) developing real time personalized dietary advice for the individual based on a current exhaled hydrogen level and the derived correlations; and i) communicating the personalized dietary advice to the individual.

FIG. 1 schematically illustrates an embodiment of a care management system 100 for providing personalized care management plans for individuals with digestive complications. The system 100 includes: a sensor device 110, a processing unit 120, a platform 150 in communication with the sensor device and the processing unit, and a portal 270 configured to maintain an interactive user database for one or more authorized users of the portal.

Processing Unit

The processing unit 120 stores a number of software applications executable by the processing unit. The software applications include a data extraction and analysis application that extracts, identifies and links associated processed data from a knowledge module and external data sources. The data extraction applications include inference engines and other algorithmically based applications that it uses to identify and correlate relevant information in a personalized database and external data sources.

In one embodiment, the processing unit 120 can include a multitude of interrelated elements. Embodiments of the processing unit can be implemented to some extent as software modules installed and running on one or more processing systems, such as servers, workstations, tablet computers, PCs, and so on. The processing unit 120 may include at least one computer processor as well as a knowledge module 220 and a data repository 210. An application program interface (API) is code that allows two software programs to communicate with each other. The API defines the correct way for a developer to write a program that requests services from an operating system (OS) or other application. A suitable interface can be used to edit the knowledge module; for this purpose, the interface exposes a set of APIs in corresponding libraries. These APIs allow submitting commands for adding, removing, or updating of data in the knowledge module.

Knowledge Module

The knowledge module 220 differs from a standard database since in this case further knowledge or informational data may be derived from existing knowledge using inference, analysis, crowd sourced wisdom and continual monitoring data from a personalized database of the client. Thus, the knowledge module is a "care" analysis engine that its data in the data repository 210. The data repository can include one or more databases that communicate with the knowledge module. The knowledge module can also receive data from an external data sourced database. The external sourced database may include data from various sources, such as laboratories, insurance companies, hospitals/clinics, media companies, 24/7 call centers/caregivers, account administrators, and other sources. The data from the external database can be extracted and transferred to the knowledge module using dynamic APIs.

The processing unit 120 processes information accessed and derived by the knowledge module to determine personalized clinical and nutritional decision analytics for clients or individual system participants. The processing unit 120 may include one or more algorithms that provide both content and personalized rules to provide feedback to the user in real time. For example, the processing unit 120 may include code for predicting trends based upon the client's personalized health profile and preferences. The information and analyses may be stored in a personalized client database and accessed by the knowledge module.

The processing unit 120 can represent one or more general-purpose processing devices such as a microprocessor, central processing unit, or the like. More particularly, the processor may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also be one or more special-purpose processing devices such as an application specific integrated circuit (ASIC), a field programmable gate array (FPGA), a digital signal processor (DSP), network processor, or the like. The processor can be configured to execute instructions for performing the operations and steps discussed herein.

Data Repository

The data repository 210 stores all the information sent to the processing unit, as well as all the data analyzed and correlated by the knowledge module. The data repository includes a database comprising a specific client's related data (i.e., a personalized database), as well as relevant data from external data sources. The data repository can be a local storage unit or a remote storage unit. The data repository may be a magnetic storage unit, optical storage unit, solid state storage unit or similar storage unit. The database can be a monolithic device or a distributed set of devices.

A personalized database is created from or based on the data captured related to a specific client. One example of such data is a client's medical records such as their medical history, laboratory data, diagnoses, treatment plans, and their family's medical history. Another example of such data is data measured by one or more biodata or sensor devices 110. Biodata or sensor devices 110 typically collect physical information or measurements of an individual user. These devices are often equipped with the necessary software to process the data generated by the device into numerically based structured data and to communicate the collected structured data to the personalized database and processing unit 120. Examples of such biodata devices 110 include glucometers, hydrogen or methane sensors, temperature sensors, heart rate monitors, blood pressure monitors, and activity sensors with tri-axis or multi-axis accelerometer chips.

One important component of the personalized database is that it is composed of data gathered from an analysis of the intestinal microbiome of the client. The presence or overabundance of certain types of bacteria have been reported to contribute to obesity, inflammatory bowel diseases, irritable bowel syndrome and other inflammatory or autoimmune conditions. An analysis of the client's intestinal microbiome is obtained from a client's fecal sample. The results of the client microbiome analysis is compared to healthy profiles to identify certain imbalances leading to a client's chronic digestive discomfort or other symptoms.

The personalized database will also include individualized insights gained by understanding the client's social structure, daily routines and cultural background to assist in understanding how that person copes with a chronic condition or symptoms on a daily basis. This type of data is vital to finding personalized treatment plans that a person will adhere to and that will provide positive changes in a person's quality of life.

Although people share the same disease or the same chronic symptomology, their ability to navigate through the symptoms often will include personal adjustments to their daily routines. Many people facing chronic diseases and associated uncomfortable or embarrassing symptoms will try alternative approaches that they are unwilling to share with their physicians. Thus, a great deal of relevant information does not appear in their medical records or in any of the data normally used to map treatment plans or other health care advice. Often these alternative approaches will include herbal remedies, supplements, acupuncture or acupressure, reflexology, relaxation techniques, or exercise regimes such as yoga or stretching.

An External Source Database.

External data sources are defined herein as data sources that are not maintained or controlled by the care management system's administrator. The internet will be routinely searched by the care management system's professionals for information from numerous blogs and other sites containing information related to the health and wellness of people with certain diseases and/or symptomology as well as laboratory or clinical sites, insurance companies, media companies, call centers, care providers, account administrators, durable medical equipment (DME) suppliers, and other sources. The external source database will also include an analysis of updates captured from crowd wisdom by including an analysis of thousands of daily logs of thousands of the care management system participants. The collective wisdom of thousands of users captured within these daily medical narratives and personal experiences will be processed using various algorithmic based data extraction applications. Capturing crowd wisdom on numerous variations in health treatments (such as the role of diet, exercise, and/or alternative health approaches) on the general well being of participants with common symptomology and chronic conditions will benefit all participants.

Internet usage data is defined herein as the client's, as well as other system participants', internet usage patterns. The internet usage patterns of system participants will be assessed for the information that the system participants with common health conditions are searching on the internet to derive their use patterns, what sites they are searching, their personalized likes and dislikes, their internet inquiries, and their downloaded information. For example, users may search for information on certain drugs/supplements, people with the same disease or similar symptoms, or new treatment plans. Information will also be derived from the sequence of user searches and the temporal associations of their searches by mapping the transition and time between searches.

The information derived from analyzing system participants internet searches and the blogs that they read and contribute to will be correlated with the daily medical narratives of users with similar diseases or symptomology to enhance the data input to be processed by the processing unit. For example, a system participant's "search" pages can be considered in personalizing their profile as reflecting their inner consciousness. In addition, the temporal associations of their search can assist in mapping patterns and probabilities of symptom recurrences and the temporal relationship of such recurrences.

Intestinal Microbiome Analysis

One important component of the care management system is data gathered from an analysis of the intestinal microbiome of the client. Initially the client will submit a fecal sample for a microbiome analysis that identifies and quantifies the diverse bacterial population of the client's gut. An analysis of the client's intestinal microbiome is obtained from a client's fecal sample. The results of the client microbiome analysis is compared to healthy profiles to identify certain imbalances leading to a client's chronic digestive condition of symptoms.

In humans, the gut contains the largest numbers of bacteria and the greatest number of species of bacteria than other areas of the human body. An individual's general health and well being is dependent on the proper balance of the bacterial populations in the gut. Imbalances in the intestinal bacterial flora are associated with a number of digestive and immunological disorders. The presence or overabundance of certain types of bacteria have been reported to contribute to obesity, inflammatory bowel diseases, irritable bowel syndrome and other inflammatory or autoimmune conditions.

The gut microbiome is increasingly being recognized as a key site of metabolism for drugs and other xenobiotic compounds that are relevant to human health. The gut microbiome has both direct and indirect effects on drug and xenobiotic metabolisms, and this can have consequences for both efficacy and toxicity. Indeed, microbiome-driven drug metabolism is essential for the activation of certain prodrugs, for example, azo drugs such as prontosil and neoprontosil resulting in the release of sulfanilamide. In addition to providing a major source of reductive metabolizing capability, the gut microbiome provides a suite of additional reactions including acetylation, deacylation, decarboxylation, dehydroxylation, demethylation, dehalogenation, and importantly, in the context of certain types of drug-related toxicity, conjugates hydrolysis reactions. In addition to direct effects, the gut microbiome can affect drug metabolism and toxicity indirectly via, for example, the modulation of host drug metabolism and disposition and competition of bacterial-derived metabolites for xenobiotic metabolism pathways. Also, of course, the therapeutic drugs themselves can have effects, both intended and unwanted, which can impact the health and composition of the gut microbiome with unforeseen consequences. The molecular complexity of the gut microbiome revealed by recent metagenomic studies has highlighted the need for correlating the drug microbiome metabolic activity and its affect on drug metabolism and toxicity.

Fecal Sampling Kit

Figure 3:
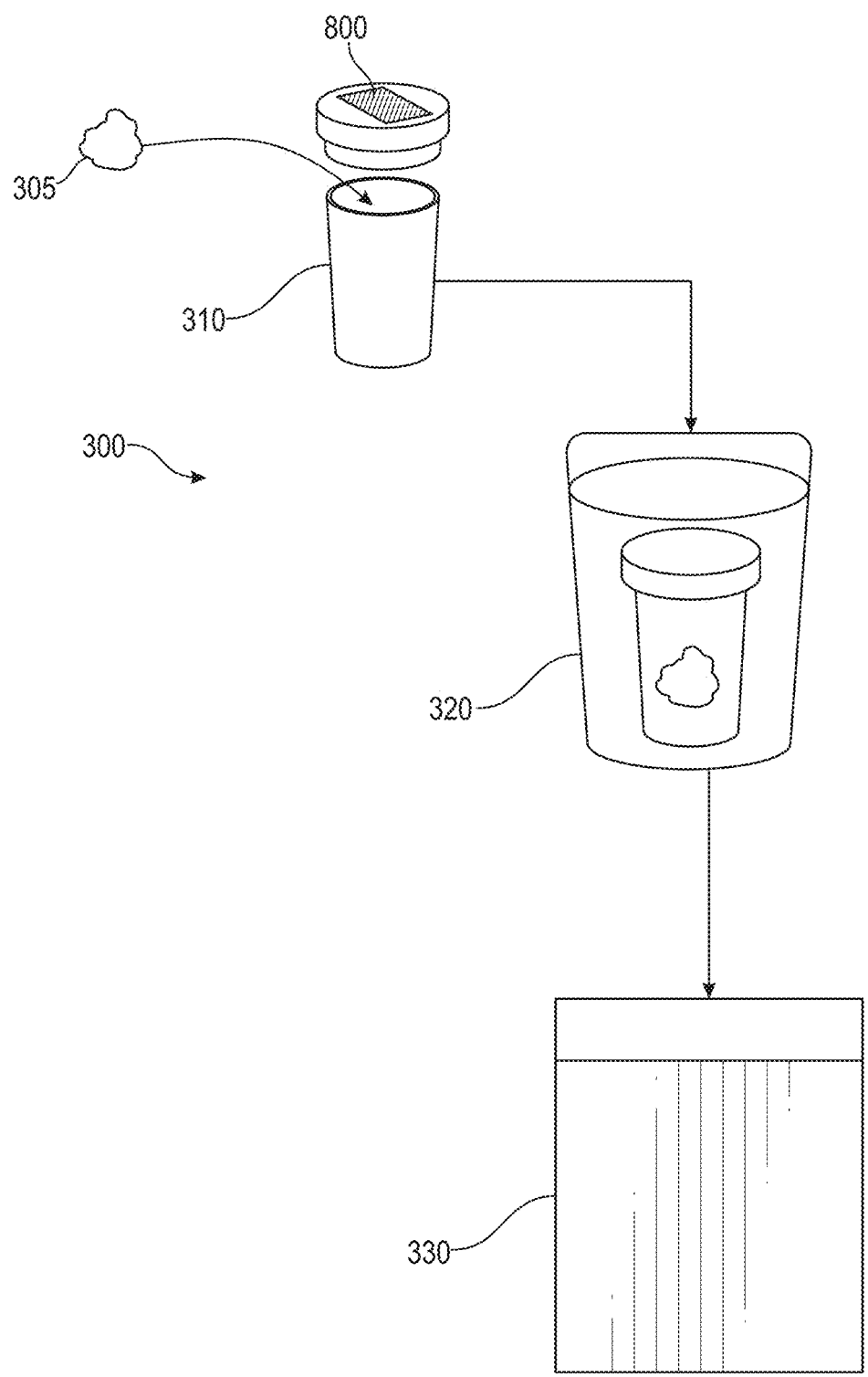
FIG. 3 is an illustration of a fecal sampling kit.

The client will use a fecal sampling kit 300, such as the one shown in FIG. 3, to submit a fecal sample 305 for a microbiome analysis. The fecal sampling kit includes a fecal sample container 310, an optional scalable stool culture bag 320, and a delivery package 330 for delivering the fecal sample to a laboratory for an intestinal microbiome analysis. The fecal sample 305 is collected and placed into the fecal sample container 310. If a culture collection swab is used to collect the fecal material, the swab should be placed in the fecal sample container 310.

Optionally the fecal sampling kit may also contain a sealable air and liquid impermeable bag 320 that the fecal sample container is placed into. The fecal sample container is placed into a delivery package 330 for mailing to a laboratory for analysis. In one embodiment of the care management system, the client will collect a fecal sample at selected time intervals. The collection of multiple fecal samples will allow changes in the measured levels of hydrogen and/or methane to be correlated with changes in the intestinal microbiome. The processing unit will also be able to correlate the microbiome changes with levels of symptomology, the effectiveness and dosage of therapeutic drugs, the dietary changes of the client, and other personalized information.

The Sensor Device

The sensor device 110 is either a hydrogen sensor 230 or a methane sensor device used to measure the digestive activity of an individual. Measuring the hydrogen or methane levels of a person measures the metabolic activity of the gut microbiome of the person. Each measurement of the level of exhaled methane or hydrogen may be processed by a processor within the device before being further communicated to the processing unit 120. Either a hydrogen or methane sensor device may be used as the sensor device 110.

Figure 4:
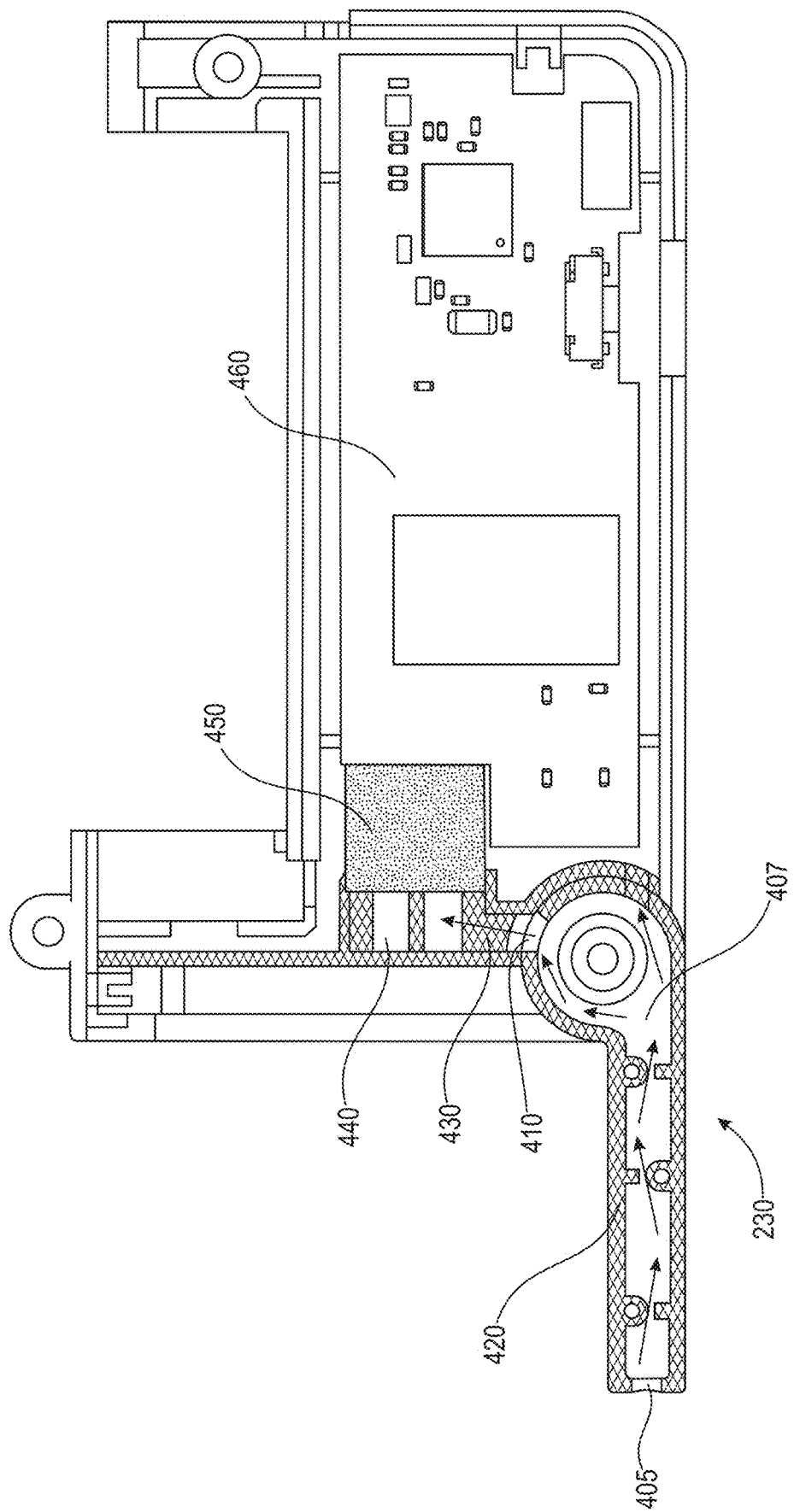
FIG. 4 is a cross-sectional view of a hydrogen sensor device.

One embodiment of a hydrogen sensor device 230 is shown in FIG. 4. The hydrogen sensor device 230 analyzes hydrogen concentration in a human breath sample to better than 5 ppm resolution. To use the sensor device a user must switch on the drive, allow a 10 second warm up, and then blow into the mouthpiece 420 for about 5 seconds. The person places their lips over and exhales into a distal end of the mouthpiece 420. The distal end of the mouthpiece has a breath entry port 405 that allows the breath to flow through an airflow channel 407. The proximal end of the mouthpiece has an exit port 410 that allows the exhaled breath to enter the flow section 430 of the airflow channel. The flow section 430 has at least one air vent 440 to allow the breath to pass through the flow section by the hydrogen sensor 450. As the breath passes by the hydrogen sensor 450, the hydrogen level in the breath is measured. To obtain repeatable exhaled hydrogen level measurements, the airflow channel to the sensor must be laminar, free of liquids, suitable for all persons, and repeatable from blow to blow. These aims are achieved with a mouthpiece that has a 2-hole exit structure allowing liquids to fall out of the airflow and gas to pass at a reasonably constant pressure by the hydrogen sensor 450. Air pressure regulating holes assist in maintaining flow at a constant rate from the user's breath.

Another embodiment of a hydrogen and/or methane sensor device 800 is shown in FIG. 3. In this embodiment the hydrogen and/or methane sensor device is embedded with the lid of the fecal sample container 310. When the hydrogen and/or methane sensor device is embedded in the lid of the fecal sample container, the sensor will detect the level of methane and/or a hydrogen that is emitted from the collected fecal sample and is correlated with the microbiome of that fecal sample. Preferably the hydrogen and/or methane sensor device 800 has a methane sensor, but may or may not include a hydrogen sensor as well. If a hydrogen sensor is included in the sensor device 800, it will allow the client to compare the levels of exhaled hydrogen levels with the level of hydrogen and methane off gassed from specific fecal samples and microbiome data.

If multiple fecal samples are collected, using measurements of off gassed hydrogen and methane will allow changes in the measured levels of hydrogen and/or methane to be directly correlated with changes in the intestinal microbiome. The processing unit will also be able to correlate the microbiome changes with levels of symptomology, the effectiveness and dosage of therapeutic drugs, the dietary changes of the client, and other personalized information.

Polysaccharides, such as glucose or lactose, are generally absorbed by the small intestine such that only a small amount of hydrogen is produced from limited amounts of unabsorbed carbohydrate metabolized by intestinal bacteria. However, malabsorption of the carbohydrate and/or small intestinal bacterial overgrowth lead to increased amounts of hydrogen or methane being produced by bacterial metabolism. The increased hydrogen/methane is absorbed through the wall of the small and/or large intestine into the blood stream. The hydrogen containing blood travels to the lungs where the hydrogen is released and exhaled, whereas the methane is generally released as flatulence. Thus the amount of hydrogen detected in the breath indicates the metabolic activity of the gut microbiome.

Obtaining the identity and quantity of a person's intestinal microbiome and the quantity in ppm of that person's exhaled hydrogen taken at the same time that the fecal sample for the microbiome analysis was taken provides a base level of exhaled hydrogen and can inform a person's understanding of future quantifications of exhaled hydrogen for that person and its relationship to that person's eating behavior and choices. A standardized exhaled hydrogen level, the exhaled hydrogen level after a consumption of a standardized dose of a specific carbohydrate by the person. For example, standardized doses of 20-150 gm of glucose, lactose, or fructose may be used to detect the malabsorption of a specific carbohydrate. Correlating the base level exhaled hydrogen, one or more standardized exhaled hydrogen levels, and data on the intestinal microbiome can assist a person to identify environmental factors (e.g. cleaners, pesticides, and herbicides that can effect bacterial populations) and medicines/nutritional supplements that have bacterial interactions and to inform the person of dietary selections that can maximize beneficial bacterial populations and limit potentially harmful populations.

For example, at any particular time different bacterial populations within the gut flora may be particularly active. Prior knowledge and data on the person's intestinal microbiome and history of their exhaled hydrogen levels can be analyzed to indicate that if certain bacteria are pronounced at any one time, the ingestion of specific foods will be metabolized and produce toxins that will lead to diarrhea or abdominal pain.

The processing unit 120 and the platform 150 may also be in communication with additional sensor devices. Examples of such sensor devices include a glucometer, a temperature sensor, a heart rate monitor, a blood pressure monitor, or a multi-axis accelerometer chip.

Platform

The platform 150 is searchable and downloadable by a client or authorized user through a mobile device such as a smart phone or through a computer. Typically, a software application available for download through app stores or distribution platforms will instruct and configure interactive communication between the combined information system and a smart phone, a tablet computer, or any other programmable computing unit.

A computerized platform 150 communicates with the processing unit 120 and its data repository, a web-based portal, mobile applications and authorized users of the care management system. By way of example and not limitation, a care management software application running on a mobile device periodically receives real-time information and suggestions via a user sub-portal. Such information and suggestions have been analyzed from the relevant data received by the platform from the knowledge module 220 and the data repository 210.

Figure 5:
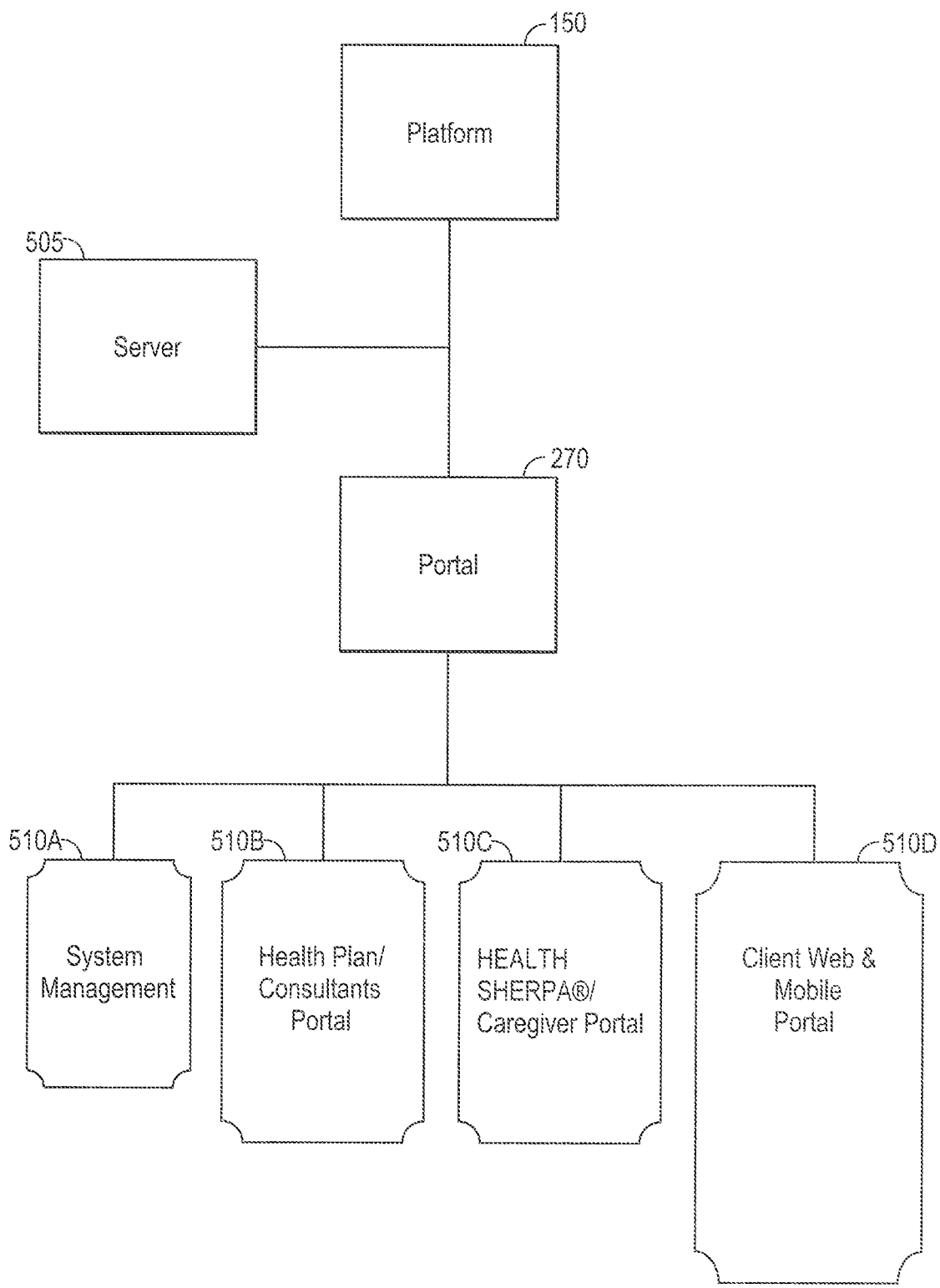
FIG. 5 is an illustration of a platform and a portal with its sub-portals that communicate with the platform of the care management system.
Figure 6:
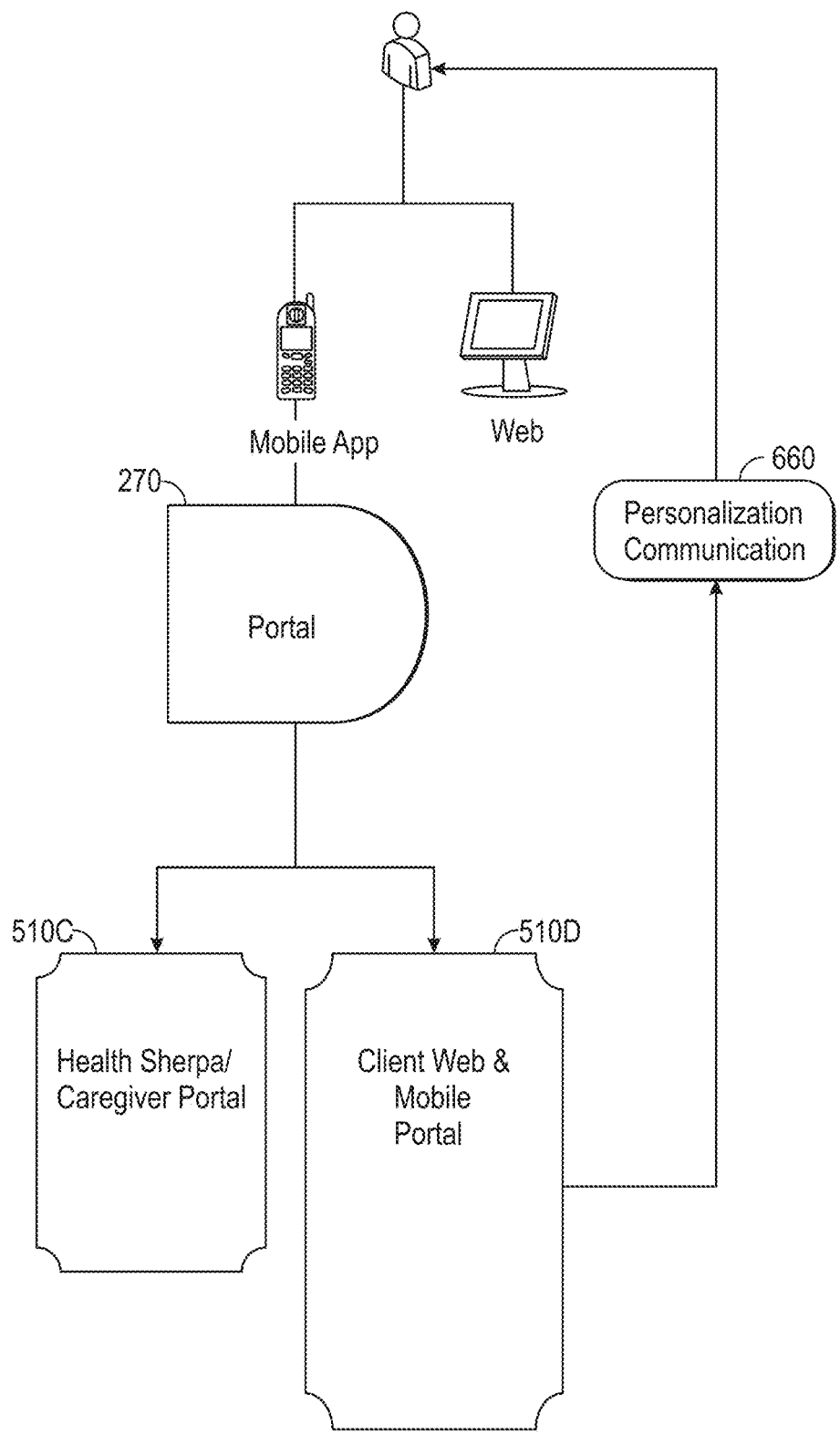
FIG. 6 is an illustration of a communication system between the client, the client sub-portal and other parts of the care management system.

FIGS. 5 and 6 illustrate an interactive platform for personalized care management according to an embodiment of the present disclosure. The platform may have a secure server 505 and a portal 270. The portal 270 provides one or more interfaces for reporting and displaying the data from the platform to the authorized system users as well as support personnel via various sub-portals, each sub-portal having restricted access.

The platform 150 can include a multitude of interrelated elements. Embodiments of the platform 150 can be implemented to some extent as software modules installed and running on one or more processing systems/computers, such as servers, workstations, tablet computers, PCs, personal digital assistants (PDAs), smart phones, and so on. The processing systems may include at least one computer processor as well as a memory (not shown). The platform may also include a special interface device that can accommodate a number of different wireless and hard wired devices similar to a "switch" box. The platform processor may be the same or similar to that of the processing unit 120 and may include a knowledge module like that of the processing unit.

The platform 150 is in communication with the data repository of the processing unit 120. The data repository includes a database comprising a specific client's data and related data from other system participants, as well as external data sources. The software applications on the processing unit include data extraction and analysis applications that extract, identify and link associated processed data from the data repository. The data extraction applications include inference engines and other algorithmically based applications that it uses to identify and correlate relevant information in a personalized database and external data sources.

The Personalized Care Management System

The data extraction applications on the processing unit 120 identify and correlate relevant information in the personalized database and external data sources and communicate that information with the platform 150. The platform processor may include software applications with instructions to implement one or more rules. For example, the rules may pertain to a daily meal or activity plan for the client, a matching of the client to either a person or a team of people to serve as the client's coach or health guide (a Health Sherpa®), nutrition guidance, client reports and predictions, client health profiles and video/chat sessions.

Typically, the platform processor will include code for predicting trends based upon the individual client's personalized health profile and preferences. For example, the rules may pertain to a daily meal or activity plan for the participant based on personal preferences, a matching of the client to one or more health consultants, nutrition guidance, exercise routines, general health predictions and alerts, trends and improvements in the client's health profile and video/chat sessions. Various parameters are considered in determining recommendations, educational messages, and directives to the client. The platform processor then analyzes and correlates the relevant data to determine useful information for the specific client and transmits that information to the client, including information relating to nutrition, exercise advice and treatment decisions.

In one or more embodiments, the platform 150 can facilitate the interaction between a client, a caregiver, a counselor, a financial/claims administrator and any other authorized user using a designated portal 270 or multiple sub-portals 510A-510D. Direct client interaction may come in the form of text or video messages, live support, or peer-to-peer experiential learning from the community to assist individuals in making sure the foods that taken in are compatible with their current digestive and metabolic activity. The instant feedback is based on several parameters (output, input, food, activity, nutrition) and not just one. Further connectivity allows for an immediate intervention from a care team support center should an emergency arise.

Access to the platform 150 may be controlled by a system administrator of the care management system 100. Only users with authorized credentials may be allowed access to the platform 150 through a specific sub-portal. For example, the memory may include cloud storage that stores profiles for one or more persons that define at least one of access privileges or preferences for respective system users. Access privileges may also be driven by a set of interactive rules based on health care privacy rules and/or clinical pathways.

The portal 270 is typically web-based. The portal 270 receives analyzed data content from the processing unit 120. The portal 270 provides one or more interfaces for reporting and displaying the data from the platform. The portal 270 can be used to create and display profiles of individual clients/users. The portal 270 can be used to display information on an individual client's symptomology, treatment progress, medications, nutritional status, etc. Portal access is controlled by the system administrator through established access privileges. As illustrated in FIG. 5, the portal 270 may include a number of modules or sub-portals with access specifically designated to authorized users. The portal or sub-portals can communicate with authorized users through mobile devices.

The portal 270 may include a plurality of sub-portals such as, without limitation, a System Management Portal 510A, a Health Plan/Consultant's Portal 510B, a Health Sherpa®/Caregiver Portal 510C and a Client Portal 510D. The portal 270 is configured to add contextual metadata to at least a subset of the analyzed data communicated to the platform. The contextual metadata can include one or more metatags that identifies an origin of the subset of analyzed data within the one or more sub-portals. The contextual metadata further comprises at least one of a unique identifier associated with access privileges for a particular sub-portal.

The System Management Portal 510A may be configured to receive data from the platform that is relevant to financial claims and system management. For example, the System Management Portal 510A may include aggregate HIPAA information, compliance reports, performance dashboard, client membership data and other related information.

The Health Plan/Consultant's Portal 510B may be configured to receive data from the platform that is relevant to a health plan manager/consultant. For example, the Health Plan/Consultant's Portal 510B may include personal health records, insurance related records, financial administration records, performance metrics, treatment plan options, crowd sourced data related to certain chronic conditions or symptoms and other related information.

The Health Sherpa®/Caregiver Portal 510C may be configured to receive data from the platform that is relevant to a counselor/caregiver of a client with chronic health concerns. For example, the Health Sherpa®/Caregiver Portal 510C may include clinical summaries, electronic medical records, prescription information, lab records, personal health records, general health and wellness blogs, clinical notes, clinical alerts, information on health coaching and previous coaching sessions with the person, assessment tools, intervention tools and other related tools and data. The Health Sherpa®/Caregiver Portal 510C may also have access to crowd sourced data related to certain chronic conditions or symptoms, symptom predictions, as well as the client's personal preferences and preferred treatment options.

The Client Portal 510D may be configured to receive data from the platform that is beneficial to a specific client/participant of the care management system. The Client Portal 510D (and any of the other portals 510A-C) is an interactive portal and it may be accessible from the Internet or as a mobile software application as shown in FIG. 5. The Client Portal 510D is configured to receive a plurality of information from the client and the information management system on a periodic basis. The Client Portal 510D is further configured to provide information on daily diet and exercise plans, informational videos and on-demand or scheduled chat sessions with the Health Sherpa® and caregiver team, education and feedback, personalized lifestyle and behavioral resources, progress status to goals and other related information.

Advantageously, the Client Portal 510D is configured to provide alerts and reminders. These can be transmitted to the client's mobile device or on another computing device and may be presented via application software. Alternatively, the information may be contained in text messages, electronic mail messages or other general-purpose application software resident on the mobile/computing device. The Client Portal 510D is also configured to provide real-time interventions using a personalized user profile for the user.

An interactive screen may be used to enter information for identifying a client, such as email, user id, phone, first and last names, medical condition, age, company name into the portal 270. A designated Health Sherpa®, a team of advisers and/or a caregiver may be matched with each client. Information on the Health Sherpa® may also be entered in the portal 270. Additional information such as the client's weight, height, daily diet and exercise plans, daily tasks, daily or weekly health status, stress levels, etc. may also be entered in the processing unit, the data repository and/or the platform. The portal 270 can be configured to allow the portal user (for example, a Health Plan Consultant or the Health Sherpa®) to message the client, retrieve the client profile and contacts, etc. The portal 270 may use an email authentication method, for patient authentication. Other authentication methods, such as authentication of the mobile device, are also applicable.

The specific client or user of the care management system 100 may view his/her data and communications on a mobile device. In one embodiment, the portal 270 may be accessed from the same mobile device that is configured to run a biodata device software application, such as the sensor device 110, or more specifically the hydrogen sensor device 230. Another embodiment may of the care management system may be configured to run more than one biodata device software applications.

The Client Portal 510D can be configured to facilitate a real-time messaging or chat session between the client and the Health Sherpa® or caregiver. The Client Portal 510D is configured to allow the client to schedule a chat session, determine the time of his/her next scheduled session and to access previous coaching sessions. The Health Sherpa®/Caregiver Portal may be configured to allow the Health Sherpa® designated to a specific client to determine the number of sessions in queue and to access predetermined information from previous coaching sessions with the client.

A high-security firewall (not shown) is used to provide a secure communication channel between the platform 150 and each sub-portal and any mobile applications. The system client and/or authorized users are required to authenticate themselves via an authentication layer.

The Client Portal 510D can be used to track client's preferences, especially those relating to diet and exercise. The tracking of favorites and the updating, analyses and recommendations based on a user's favorites is normally a data-intensive function. The tracking and updating of the client's favorites is generally based on information either gathered from the user at an interview, log entries, or from responses to general questionnaires. Accordingly, the tracking, updating, analyses and recommendations based on favorites are normally performed by the processing unit and/or the platform, following transmission of real-time client updates from the client's mobile device or biodata device. Thus, the constant review and analysis of an individual's general health and symptomology allows the system to personalize all treatment regimes and recommendations.

For example, the recommendations for eating can be highly specific and personalized (e.g., eat X calories of carbohydrates selected from "your favorites" mashed potatoes and pinto beans; eat X calories of lean protein, selected from "your favorites" shrimp and egg whites). Similarly, recommendations for exercise can include recommendations for exercise duration and exertion level. Exercises may also be personalized for stretching particular muscles or as selected by a physical therapist to assist persons with chronic back pain or poor knee/hip mobility.

Furthermore, messages can be sent based on suspected allergies or intolerances such as bronchial allergies to volatile compounds such as perfumes, contact allergies to soap additives or textiles, food allergies to certain foods such as shrimp or berries, or food intolerances such as milk products for lactose intolerant individuals or gluten products for colitis. Or, the client/user can be directed to stop eating after a certain time or the client may be directed to stop or start exercising based on heart rate.

The platform 150 and its ability to communicate with mobile devices and various computers or processors provides both short and long term benefits. The short term advantages of this platform may include real-time alerts or real-time feedback that includes dietary and nutritional information and liquid intake to help regulate every day health; reference to certain advantages or risks seen for certain health treatments or therapies on symptomology; aid in meeting nutrition requirements and the absorption of foodstuffs; and the enablement of individual reporting and monitoring of general health and a person's likes and dislikes.

Using the Care Management System

An individual's general health and well being is dependent on the proper balance of the bacterial populations in the gut. Imbalances in the intestinal bacterial flora are associated with a number of digestive and immunological disorders. The presence or overabundance of certain types of bacteria have been reported to contribute to obesity, inflammatory bowel diseases, irritable bowel syndrome and other inflammatory or autoimmune conditions. A client's microbiome analysis is compared to healthy profiles to identify certain imbalances leading to a client's chronic digestive condition of symptoms. Furthermore, digestive complications that include bloating, abdominal pain, increased flatulence, loose stools, constipation, and tiredness have been associated with exhaled hydrogen levels of greater than 10 ppm.

The health complications of individuals with exhaled hydrogen levels consistently above 10 ppm can be improved when that person works with health support staff to develop a therapeutic nutritional program specifically designed for that individual. Daily monitoring of symptoms and exhaled hydrogen levels encourage the person to make informed decisions about foods, supplements, and medication to balance their gut microbiome and reduce their exhaled hydrogen levels. Individuals that actively participate in the health care management system that is individualized for their heath care and dietary needs can reduce their exhaled hydrogen levels from a level that is consistently above 10 ppm to one that is consistently 0 ppm. This consistent reduction in exhaled hydrogen levels improves the person's general health and well being and can eliminate and/or reduce their digestive discomfort and symptoms.

One aspect of eliminating and/or reducing the person's digestive discomfort and symptoms is that the need for medical intervention can be reduced with less need for hospitalization or surgery. Furthermore, eliminating and/or reducing the person's digestive discomfort and symptoms can reduce the person's need for pharmacological treatment by reducing the prescribed dosage and/or frequency of a drug regimen.

Case History.

A client presented with an ulcerative colitis diagnosis and consistent pain, gas, bloating, uncontrollable and unexpected diarrhea, and severe psoriases. The client had been on a double dose of Infliximab every 6 weeks for 4 years. His debilitating symptoms caused the client to live in a constant state of anxiety and fear of catching an infection.

Figure 7:
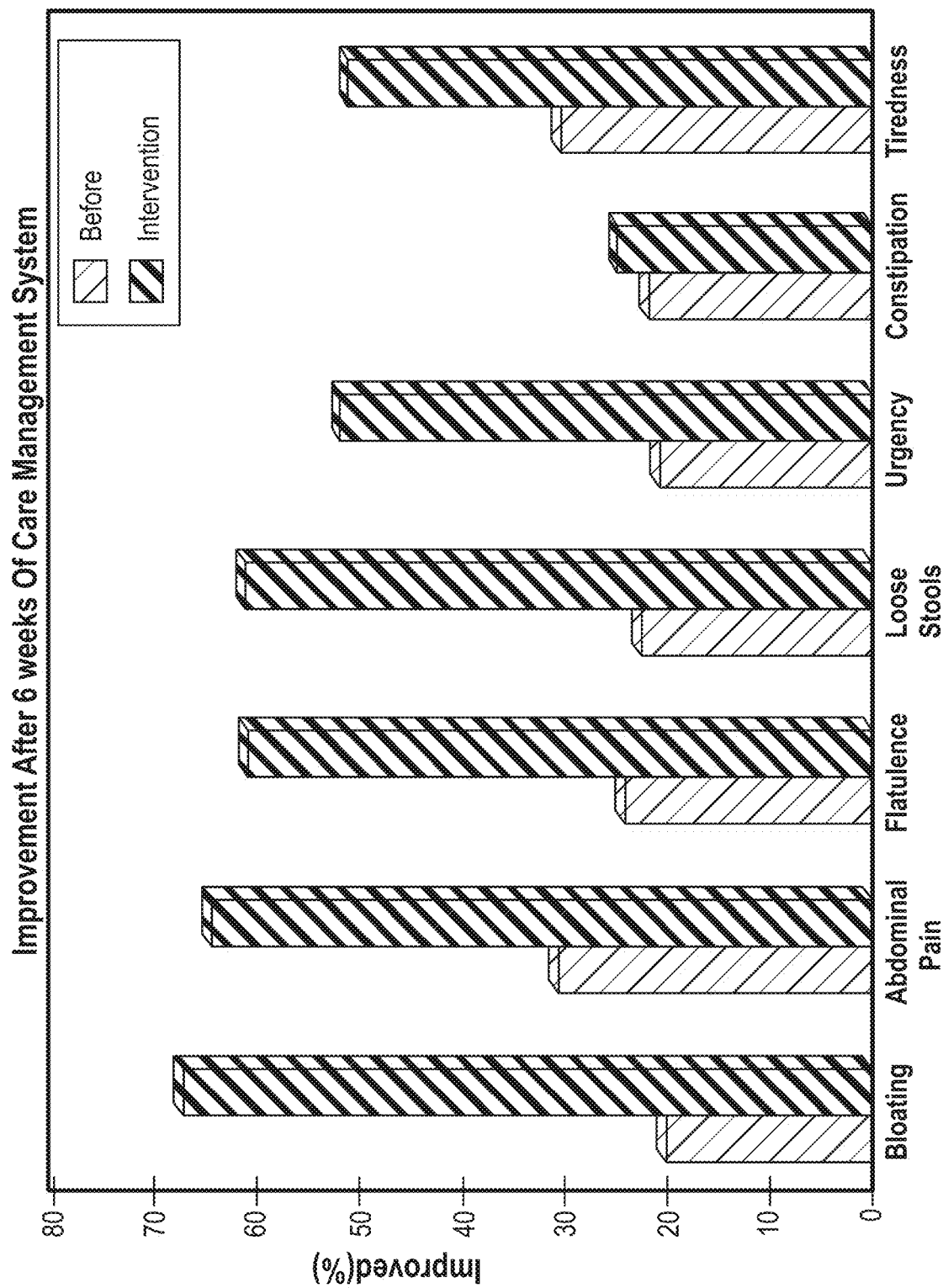
FIG. 7 is a bar graph of symptom improvement of a client on the care management system.
Figure 8B:
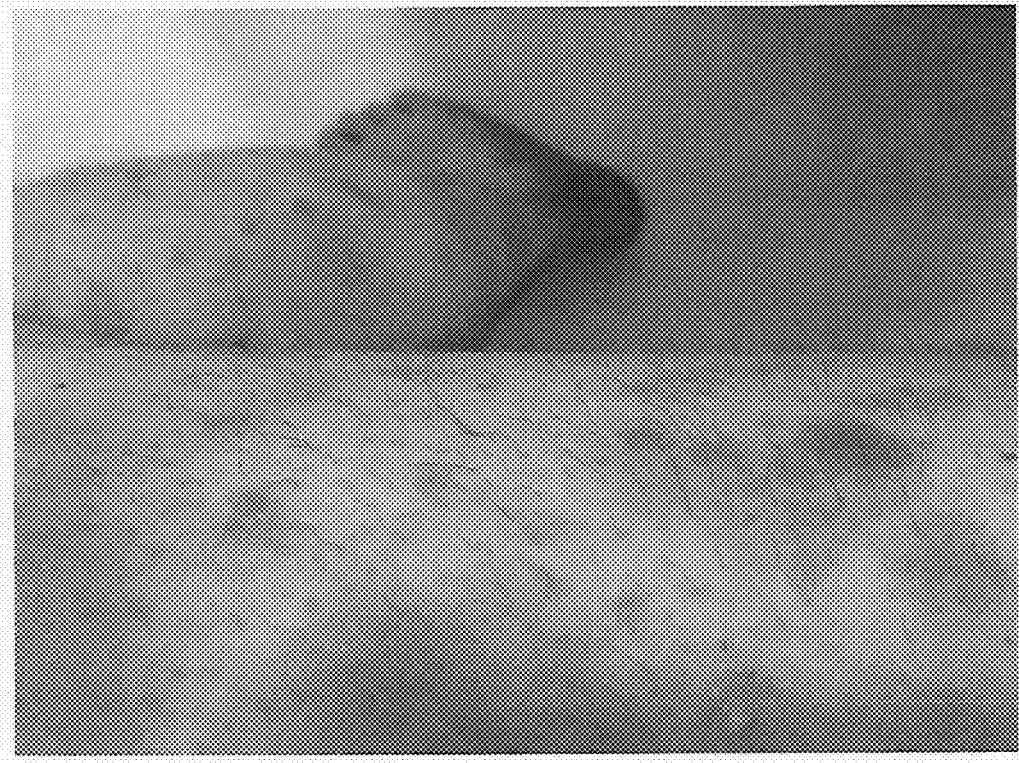
FIG. 8B is a photograph of the client's psoriasis after the client was on the personalized health care management system for six weeks.
Figure 8A:
FIG. 8A is a photograph of a client's psoriasis before the client was on the personalized health care management system.

Upon signing up for the personalized care management system, the client had his gut microbiome analyzed and frequently monitored his exhaled hydrogen level. The client worked with the assigned health care professionals to boost his self confidence and communication skills and identify a therapeutic nutrition program to inform his decisions about foods and supplements. After six weeks on the personalized care management system the client had drastically changed his gut microbiome profile and decreased his exhaled hydrogen levels to base levels. The client reduced his stress levels and reported a significant decrease in his debilitating symptoms as shown in FIG. 7. Furthermore, the client's psoriasis was substantially improved as seen in FIGS. 8A and 8B. FIG. 8A shows the client's psoriasis at the beginning of his participation in the care management system when his exhaled hydrogen levels were consistently between 10 ppm and 20 ppm. FIG. 8B shows the client's psoriasis after six weeks of his participation in the care management system when his exhaled hydrogen levels were consistently at base level or 0 ppm. As the client's symptoms and psoriasis improved, the client worked with his doctor to reduce his Infliximab dosage to one dose every 12 weeks.

What is claimed is:

1. A care management system for a person having a chronic digestive disease comprising:
   a) a breath hydrogen gas sensor or a breath methane gas sensor to measure, respectively, an exhaled hydrogen or methane level of the person;
   b) a fecal sampling container with a fecal methane gas sensor or a fecal hydrogen gas sensor configured, respectively, to measure an off gassed methane or hydrogen level from a fecal sample of the person;
   c) a processing unit in communication with the breath hydrogen or methane gas sensor and the fecal hydrogen or methane gas sensor that is configured to correlate changes in the exhaled hydrogen or methane level with the fecal off gassed methane or hydrogen level;
   d) an interactive portal in communication with the processing unit and a personalized database, wherein the processing unit is configured to provide a user interface via the portal, wherein said user interface is for collection of data about the person and the processing unit is for analysis of said data about the person to determine a state of the person's microbiome, wherein said data and said state are stored in the personalized database; and
   e) a heart rate monitor and optionally also a blood pressure monitor which communicates with the processing unit and provides heart rate and optionally blood pressure data to the personalized database, wherein the processing unit generates a message for the person to stop or start exercising based on the heart rate data.

2. The system according to claim 1, further including a delivery package for the fecal sampling container which is configured for sending the fecal sample container to a laboratory.

3. The system according to claim 1, wherein the breath hydrogen gas sensor measures the hydrogen level in an exhalation of the person.

4. The system according to claim 3, wherein the breath gas sensor includes a hydrogen detector configured to measure an exhaled hydrogen level in a breath sample exhaled into a compartment of the breath hydrogen gas sensor that flows past the hydrogen detector.

5. The system according to claim 1, wherein an exhaled hydrogen or methane level of the person is measured after an ingestion of a known quantity of a designated carbohydrate, and said hydrogen or methane level is correlated with the state of the microbiome.

6. The system according to claim 5, wherein the portal is configured to send queries to the person and is capable of receiving information from the person and analyzing the received information and is configured to provide individualized reminders, advice and coaching to the person.

7. A digestive improvement system comprising:
   a) a fecal sampling kit that includes a fecal sample container, a delivery package for sending the fecal sample container to a laboratory for an intestinal microbiome analysis, and a fecal gas sensor device configured to measure a methane or hydrogen level off gassed from a fecal sample;
   b) an intestinal microbiome analysis data derived from a laboratory analysis of the fecal sample of a person, wherein the intestinal microbiome analysis data is stored in a processing unit and, wherein:
   c) the processing unit is configured to provide an interface via a portal in communication with the fecal gas sensor device, the processing unit, and a heart rate monitor, wherein the processing unit collects data regarding the methane or hydrogen level off gassed from the fecal sample and the intestinal microbiome analysis data, and analyzes said data regarding the methane or hydrogen level and the intestinal microbiome analysis data to determine a state of the person's microbiome, and wherein the processing unit generates a message for the person to stop or start exercising based on a heart rate data.

8. The digestive improvement system of claim 7, further comprising a breath gas sensor device configured to measure an exhaled hydrogen or methane level of the person.

9. The digestive improvement system of claim 8, wherein the breath gas sensor device includes a hydrogen detector configured to measure an exhaled hydrogen level in a breath sample exhaled into a compartment of the sensor device that flows past the hydrogen detector.

10. The digestive improvement system of claim 7, wherein the processing unit is configured to receive and analyze a series of exhaled hydrogen or methane level measurements of the person and analyzes the exhaled hydrogen or methane level in said series in determining the state of the person's microbiome.

11. The digestive improvement system of claim 10, wherein the processing unit is configured to communicate real time specific dietary recommendations to the person based on the state of the person's microbiome.

12. The digestive improvement system of claim 10, wherein the processing unit is configured to receive and analyze consumed dietary selections and a digestive discomfort level in determining the state of the person's microbiome.

13. The digestive improvement system of claim 7, wherein the portal is configured to send queries to the person and is capable of receiving information from the person and analyzing the received information to provide individualized reminders, advice and coaching to the person.

14. The digestive improvement system of claim 7, wherein the fecal sampling kit includes a fecal sample container and a delivery package for sending the fecal sample container to a laboratory for the intestinal microbiome analysis.

* * * * *